United States Patent
Severance

(10) Patent No.: US 6,821,116 B2
(45) Date of Patent: Nov. 23, 2004

(54) SYSTEM FOR SCANNING ORAL ENVIRONMENT

(75) Inventor: Gary L. Severance, Jupiter, FL (US)

(73) Assignee: Ivoclar Vivadent, Inc., Amherst, NY (US)

( * ) Notice: Subject to any disclaimer, the term of this patent is extended or adjusted under 35 U.S.C. 154(b) by 0 days.

(21) Appl. No.: 09/950,435

(22) Filed: Sep. 12, 2001

(65) Prior Publication Data

US 2003/0049585 A1 Mar. 13, 2003

(51) Int. Cl.[7] .............................. A61C 3/00; A61C 19/10
(52) U.S. Cl. ........................................... 433/29; 433/26
(58) Field of Search ............................ 433/29, 26, 140; 396/16

(56) References Cited

U.S. PATENT DOCUMENTS

| | | | |
|---|---|---|---|
| 3,812,505 A | * 5/1974 | Elliott | 433/29 |
| 4,654,794 A | 3/1987 | O'Brien | 364/413 |
| 4,836,674 A | 6/1989 | Lequime et al. | 356/319 |
| 5,177,694 A | 1/1993 | Graham et al. | 364/526 |
| 5,659,625 A | 8/1997 | Marquardt | 382/118 |
| 5,766,006 A | 6/1998 | Murljacic | 433/26 |
| 5,851,115 A | 12/1998 | Carlsson et al. | 433/215 |
| 5,867,588 A | 2/1999 | Marquardt | 382/118 |
| 5,961,324 A | 10/1999 | Lehmann | 433/26 |
| 6,038,024 A | 3/2000 | Berner | 356/326 |
| 6,093,019 A | 7/2000 | Morandi et al. | 433/29 |
| 6,132,210 A | 10/2000 | Lehmann | 433/26 |
| 6,206,691 B1 | 3/2001 | Lehmann et al. | 433/26 |
| 6,210,159 B1 | 4/2001 | Lehmann et al. | 433/26 |
| 6,244,865 B1 | * 6/2001 | Nelson et al. | 433/140 |
| 6,386,867 B1 | * 5/2002 | Durbin et al. | 433/31 |
| 2002/0058229 A1 | * 5/2002 | Sugimoto | 433/29 |

* cited by examiner

Primary Examiner—Todd E. Manahan
(74) Attorney, Agent, or Firm—Nixon Peabody LLP

(57) ABSTRACT

The invention relates to a system and method for scanning a plurality of teeth and gums in a patient's mouth. The system includes a mouthpiece, a camera that fits in the mouthpiece, and an electronic storage medium. The camera can move in an arc within the mouthpiece to preferably scan the entire mouth of the patient and is preferably connected to or includes a CD, DVD, a computer hard drive, or electronic diskette to save the image for later use. The image can then be compared to a patient's prior image or compared to a dental standard to determine the patient's dental health and cosmetic characteristics.

22 Claims, 1 Drawing Sheet

SYSTEM FOR SCANNING ORAL ENVIRONMENT

FIELD OF INVENTION

The invention relates to methods and devices for scanning an oral environment. More specifically, the invention relates to a computer-based system for scanning and analyzing images of the mouth for storage and comparison to known images and prior images of the same patient.

BACKGROUND OF THE INVENTION

There has been as shift in recent years in dentistry from a philosophy of drilling and filling teeth to one of prevention and cosmetics. Many serious dental health problems can be treated or prevented if detected early. Such detection relates to the appearance and color of the teeth and gums. Due to concerns about the visual appearance of their teeth, many people also undergo clinical procedures to enhance their smiles or to correct certain defects. Such clinical or cosmetic procedures of this type generally involve the modification of tooth shape, alignment, and color.

The appearance, i.e., color and texture, of the gums provides an indication about a patient's dental health. If the gums are red or swollen, this may indicate the onset of gingivitis or other gum disease. Dental professionals (e.g., dentists, hygienists) presently "eyeball" the teeth and gums to determine whether or not there are any health issues. The dental professional may record on the patient's chart that the gums appear "pink" or "red." At the patient's next visit, the dental professional may notice that the gums still appear red, or that they appear more red or pink. It is difficult, however, to determine whether the color or visible texture of the gums has changed, e.g., are the gums more or less red than the previous visit, or are they different in some other way. The dental professional may have seen numerous patients since a particular patient's last examination and may not remember the precise color of the gums of the particular patient. This is made further difficult because the gum color is usually a shade of pink or red and descriptions are subjective.

As a person ages or as disease progresses, the gum tissue will often recede from the teeth. This condition may result in bone loss. The level of the gum-line can also indicate whether the gums, the tooth, or even the underlying bones are healthy, especially when compared to the previous level of the gum-line to determine whether it has receded. The dental professional may attempt to measure the level of the gum lines with a measuring device placed along the tooth structure. Gingival height is typically measured from the incisal edge of the tooth to the gum tissue. This technique is very imprecise for measuring as different dental professionals may measure slightly differently, and the same dental professional may even measure slightly differently on different days from different spots. This makes comparison to a standard or to the patient's previous measurement inaccurate or difficult at best.

There is also a trend in dentistry in that many patients desire cosmetic treatments to modify tooth alignment, size, and color. It may be necessary to reduce the tooth size or to increase the size with porcelain laminate veneer. The existing protocol for these procedures requires the dental professional to take an impression of the patient's teeth and construct a replica of the teeth from the impression. The dental professional then measures the replica using a ruler or similar device to get the size of the teeth and their position and relationship to each other. The dental professional must then perform calculations to determine the proper treatment. While certainly better than an "eyeballing" technique, this procedure still lacks precision. Each dental professional may measure the teeth in a slightly different way, so that the data are not reproducible when the patient visits different dental professionals. Other sources of potential error include faulty or out-dated equipment.

Patients may also desire to change the shade of their teeth, generally by whitening or otherwise brightening them. A necessary first step in this regard is to determine the shade of the existing teeth. The goal may be to whiten all of the teeth to a certain predetermined shade, or it may be to match the shades of some of the teeth to the others. Currently, the dental professional will utilize a standardized shade guide, such as VITA™, BIOFORM™, and CHROMASCOP™. These guides are generally used in a rudimentary fashion. The guide itself is a plastic plate with color tabs that are shaped like teeth. The dental professional holds one or more of the tabs up to the patient's tooth and visually determines the closest match. There is a great deal of subjectivity involved in such a measurement and the dental professional may not be sufficiently skilled or qualified for the task. The lighting and ambient light in the room can also affect selection of the tooth shade.

The current method of recording these data is that the dental professional typically writes his findings on the patient's chart. Not only does this method present the problems of subjectivity of the measurement and difficulty in comparing one visit with the next, the lack of precision of language can present challenges for the dentists and their assistants. This is especially true if a patient sees a different dentist or a different hygienist is reading the chart for a subsequent examination. This is not a problem with certain measurements, such as x-rays, that are kept in the patient's file and can be read by any dental professional without the need for remembering and interpreting prior subjective measurements and imprecise language.

U.S. Pat. Nos. 5,766,006, 5,961,324, 6,132,210, 6,206,691, and 6,210,159 disclose systems and methods for determining tooth shades by comparing those shades to standard shades. This information can be used to more accurately determine a patient's tooth shade and correlate this to the standard for changing the shade of the tooth. The systems and methods of these patents are generally intended for use in connection with the restoration of a single tooth, rather than for monitoring the patient's entire mouth.

Thus, there is a need for a system for obtaining dental information from a patient wherein reliable, reproducible information is obtained regarding the color and orientation of the patient's teeth, as well as the color and position of the patient's gums with respect to the teeth, and for saving the data in a format from which they may be readily retrieved and used in the future. There is also a need to use these data for comparison to standardized guides for tooth and gum health, as well as for tooth size, shape, shade, and other information. The present invention provides these and other features in a manner which is not heretofore known in the art.

SUMMARY OF THE INVENTION

The invention relates to an apparatus for scanning an oral environment including a mouthpiece, a scanning device disposed within the mouthpiece for capturing one or more images of the oral environment, and an electronic storage device for storing each image of the oral environment. The storage device is connected to the scanning device, which will preferably include a camera capable of moving within the mouthpiece.

The device may further include one or more mirrors slidably or rotatably attached to the mouthpiece to redirect images at various angles into the scanning device. The electronic storage device preferably includes a CD, a DVD, digital tape, a computer hard drive, a flash card, a smart card, or an electronic diskette. In another embodiment, the electronic storage captures each image for storage on photographic paper or negative. For this embodiment, the storage device comprises a computer and associated printer. The mouthpiece includes a tab for a patient having teeth to bite on to temporarily hold the apparatus adjacent the patient's teeth. A track is typically included in the mouthpiece on which the scanning device moves. The apparatus may also include a monitor to display the captured image.

The invention also relates to a method of obtaining and manipulating an electronic image of a plurality of a patient's teeth including scanning the plurality of teeth to provide a first electronic image that includes at least one dental characteristic of gingival color, gingival height, tooth color, tooth height, or tooth width of each tooth of the plurality of teeth, and transferring the first electronic image to an electronic storage device. The method may further include scanning the plurality of teeth to provide a second electronic image that includes at least one dental characteristic of gingival color, gingival height, tooth color, tooth height, and tooth width of each tooth of the plurality of teeth and comparing the at least one dental characteristic of the second electronic image to that at least one dental characteristic of the first electronic image. The method may further include comparing the dental characteristic of the teeth of the first electronic image with the same dental characteristic in a dental standard image. Preferably, these comparisons are performed electronically. The method may also include calculating the ratios of the widths of at least two of the plurality of teeth in the first electronic image with respect to each other. The method may also include matching the tooth color of at least one tooth of the first electronic image to the color of an adjacent or contra-lateral tooth to facilitate restoration of the at least one tooth.

In anther embodiment, the method also includes scanning a preparation to determine the color of the preparation and provide a second electronic image and matching the color of the preparation in the second electronic image to the tooth color of the first electronic image. Preferably, the scanning is performed by a camera and the electronic storage device includes a CD, a DVD, digital tape, a computer hard drive, a flash card, a smart card, or an electronic diskette. Preferably, the image may be displayed on a monitor and the displaying is concurrent with the transferring to the electronic storage device.

BRIEF DESCRIPTION OF THE DRAWING

The invention will be better understood in relation to the attached drawings illustrating preferred embodiments, wherein.

DETAILED DESCRIPTION OF THE INVENTION

Figure 1:
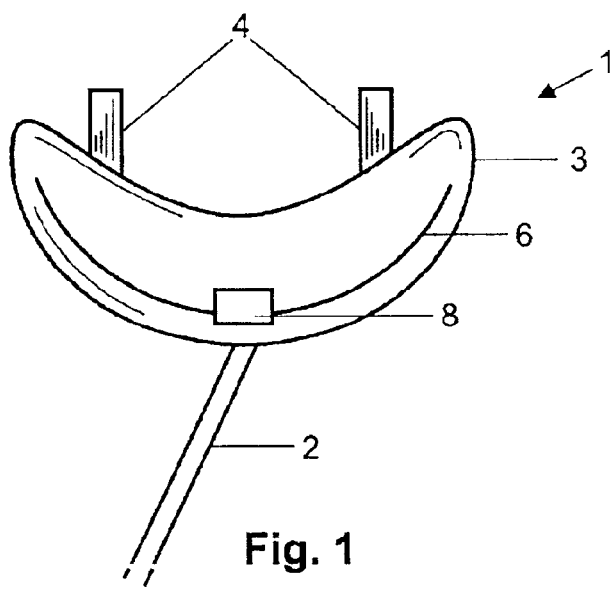
FIG. 1 shows a cross-sectional view of the invention.
Figure 2:
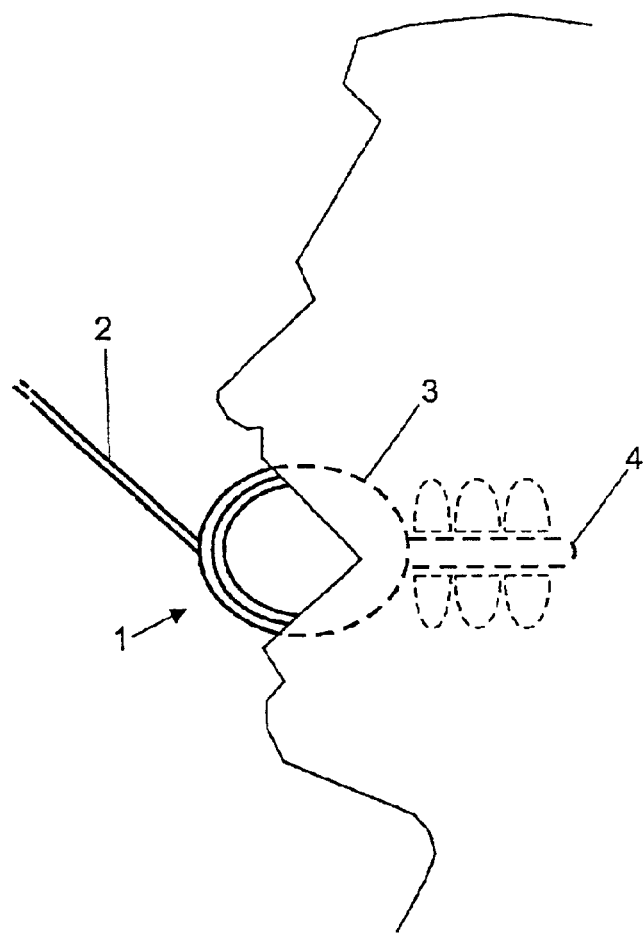
FIG. 2 shows a partial cross-sectional view of the invention in place in a patient's mouth.

The invention relates to a system and method for simultaneously scanning at least two teeth of a patient. Preferably, the scan will encompass at least the smile of the patient, i.e., the visible zone of the teeth, the front 8 upper teeth and the front 8 lower teeth. More preferably, the scan will encompass the entire upper or lower mouth of the patient, or both. The image should more preferably capture both the lower and upper teeth in a single scan. Cameras that may be adapted for use according to the present invention are commercially available from companies such as Sony Corporation of Tokyo, Japan, which capture electronic images on recordable CDs.

Referring to the drawings, the device 1 includes a camera 8 fit into or formed into a mouthpiece 3 that fits inside the patient's mouth. The mouthpiece 3 may include one or more tabs 4 for the patient to bite on to secure the mouthpiece 3 in place. The camera 8 can then move along a track 6 and scan back and forth in an arc, around the length of the mouthpiece 3 and across the buccal side of the patient's teeth. In this way, the camera 8 can capture the image of the teeth and gums. The device 1 may alternatively include mirrors that move within the mouth around the camera lens to help to capture images of the teeth and gums that the camera 8 could not otherwise scan or to capture a full can of the mouth. In one embodiment, the camera is stable within the mouthpiece, while the mirrors move along the track 6. In one embodiment, the image is stored on CD or other electronic media housed in the camera for later use. Alternatively, an electrical cord 2 connects the camera 8 to an electronic storage device, discussed below. The camera can be secured at the end of a tab and rotates on its axis as it scans the teeth.

The camera may operate in low ambient light or may include one or more light sources to facilitate a sharp image. The light source may be any suitable source known to those of ordinary skill in the art. The source may be suitable for the camera to be used to scan the lingual side of the patient's teeth, as well as the lingual gums, if desired. For example, a small bulb can be attached to the tab away from the bite surfaces thereof. Alternatively, the light source can be mounted on the camera housing.

The mouthpiece may be made of rubber, plastic, or any other suitable materials known to those of ordinary skill in the art that are safe for use in the patient's mouth. It should be substantially rigid so as to help protect the scanning device. The mouthpiece may optionally include a positioning guide to ensure that the device is in the same position in the patient's mouth for subsequent scans. This is important for comparing subsequent images of the same patient or for comparing to standards.

Preferably, the camera could be easily removed from the mouthpiece for maintenance or repair when needed. The mouthpiece could be disposable or easily sanitized to prepare it for use by the next patient. In another embodiment, a dental dam, plastic sheet, or other protective cover can surround the mouthpiece. After use, the protective cover can be removed, disposed of, and replaced so as to minimize contamination from the scanned patient to the operator of the apparatus or a subsequent patient.

The resulting image from the scan can advantageously be displayed on a monitor or similar device in real time as the mouth is scanned. Preferably, the display is concurrent with the transfer of the image to the electronic storage device. Alternately, the display can occur after the scan is completed, and either concurrently with or subsequent to the capturing of the image by the electronic storage device. The display may be located directly in the examination room, such that the dental professional may use the display for on-the-spot diagnosis, or it may be shown in the laboratory where it may be viewed by a technician or for later viewing by the dental professional when preparing the patient's chart.

The electronic images resulting from the scan may include such information as gingival color, gingival height, tooth color, tooth height, and tooth width for the teeth that are scanned. In one preferred embodiment, gingival color and height are both imaged. In another preferred embodiment, tooth color and height are both imaged. The image can include all 4 pieces of information for the plurality of teeth, as well. Using an image from a subsequent scan, the dental professional can compare the gingival color or gingival height to the gingival color or gingival height of the prior image to determine whether these have changed. The dental professional may further compare the gingival color or gingival height to a dental standard image to assist in a diagnosis. The dental professional may also calculate the widths of the teeth in the image with respect to each other. This information can be used to properly shape the teeth. The image should show a plurality of teeth, such that the dental professional may compare the tooth color to adjacent or contra-lateral teeth to match the shade or color.

The device may also be used to scan a preparation to determine its color. The tooth color shown in the image can then be matched to this color, as desired. This matching takes into account the starting color of the teeth, such that the degree of similarity of the color of the tooth to the color of the preparation initially is taken into account when determining how to color the tooth to match the preparation color. If the tooth is very similar to the preparation color, much less shading will be necessary to match the color than if the tooth color is initially very different from the preparation color. As an example, if the teeth are stained from tobacco, such that they have a deep yellow shade, much more shading will be required to match the teeth to a bright white preparation than if the teeth are just slightly dulled from certain foods. Preferably, a suitable software package will allow these manipulations to match the color of the teeth to the color of the preparation to be performed electronically.

Since the images are an accurate, straight-on representation of the buccal surfaces of teeth, the image can be processed to enable the software to determine the exact dimensions of the tooth for the technician, thus avoiding the need to take physical measurements. The images may also be compared to standards to determine whether the teeth and gums are proportioned properly. The Golden Proportion is one such standard to determine tooth size and shape in relation to each other and to the mouth. The Golden Proportion is discussed in detail in U.S. Pat. Nos. 5,659,625 and 5,867,588, the disclosures of which are incorporated herein by express reference thereto. Using this standard, when the mouth is viewed from the front, the ratio of the width of central incisor to the width of the lateral incisor is 1.618 to 1. Likewise, the ratio of the width of the lateral incisor to the width of the canine is 1 to 0.618. Other aspects of the smile may also be in Golden Proportion to each other. The patient's teeth should also have approximately the same length. A computer facilitates to the operation of this system because it enables all these data to be stored in its memory or on a hard drive, can electronically process any of the information and can display it on a monitor for easy viewing by the dental professional or technician. In addition to matching a replacement tooth to the remaining teeth, these data can be used to determine cosmetic changes to all teeth to conform to desired optimum proportions as well as to correct any deficiencies that may later lead to dental problems. The data can further be used to compare before, after, and ideal conditions to inform the patient of progress.

The software would preferably allow the operator, i.e., the dental professional or technician, to simultaneously display multiple shots of the tooth or teeth. For example, by displaying 6 individual shots of the front 6 upper teeth, the proportions of each tooth as well as its proportion with respect to adjacent teeth can be quickly and easily ascertained. The exact dimensions of width and height of the teeth can be quickly calculated by the software and the relation of one tooth to another can be provided with suggestions for any necessary or recommended modifications. This process can be repeated with the bottom 6 teeth to provide the patient with a complete smile makeover, when desired. The display of multiple images also enables the technician to view the contra-lateral tooth to the one being restored.

The displayed images also enable the technician to generate an image of a missing tooth. When a central is missing or is defective, a lateral or contra-lateral central can be imaged and the image can be morphed into a central. The software compensates for size and slight shade differences between a lateral and a central, so that the technician will be looking at a central rather than trying to generate a central by looking at a lateral. The result is that the final restoration is much closer in shape and shade to the missing tooth than to the one used to generate the image of the missing tooth.

Advantageously, the image may also be stored in an electronic storage medium, such as a CD, a DVD, a computer hard drive, an electronic diskette, digital tape, a mini disc, flash card, smart card, or any of a number of other such storage media. Preferably, the image would be directly stored to a CD or DVD. The image can be directly stored on a card or other electronic storage medium in the camera, and then transferred to a computer hard drive, CD, or DVD after then images are obtained. In this way, the image may be conveniently saved with the patient's file and viewed at a later time, such as at a subsequent examination or for analysis by the dentist or referral specialist at a later time when the patient may be unavailable. The patient could also view the saved image to see a "before and after" effect for dental procedures, as well as to see what their teeth might look like if certain procedures were performed. This latter can be accomplished using an overlay of a dental standard coupled with the patient's scan. Suitable computer software can be used to merge the images, if desired.

The image may also be captured and/or stored on photographic paper or as a negative. In this way, still images may be printed that can be easily stored with the patient's file, or the patient may take such a picture with him should another dental professional or technician need to be consulted.

The device is portable with an electrical cord connecting the camera in the mouthpiece with the storage medium. In this way, the dental professional may easily manipulate the device. Such cameras are commercially available from, e.g., Sony Corporation of Tokyo, Japan. In another embodiment, the camera digitally records the image and stores it on a card. After the images are recorded, they are later downloaded onto the electronic storage device. In this embodiment, the electrical cord is not necessary while the device is in the patient's mouth. Rather infrared, radio frequency, or an electrical cord can be used later to capture or transfer the scan to an electronic storage device. In an additional embodiment, the device is wall mounted, similar to existing x-ray devices. The device could either be swung over to the patient who is lying in the examination chair, or the patient could stand and place his mouth on the disposable and replaceable mouthpiece.

The image could also be compared to a new image of the patient's mouth taken during a subsequent examination to determine if there are any significant changes to the patient's oral appearance, e.g., tooth color, gums, and the like, which may be analyzed by a dental professional to help determine dental health. The image may also be compared to dental standards that show progressions or symptoms of different oral and gingival diseases. The comparison could advantageously be performed electronically to increase the accuracy of such a comparison. A digital processor, such as a computer or similar device having an appropriate software package, could analyze and compare the image to determine whether further examination or treatment is needed. The processor can also be pre-programmed with the standards. In this way, the invention may be used as a learning tool for dental professionals and patients alike.

Another use of the image is to compare the image to shade and color standard guides, such as VITA™, BIOFORM™, or CHROMASCOP™ to determine the patient's tooth shade. The digital processor could then relay this information to a lab technician, where the tooth shade may be matched to the shade of the tooth to be replaced, or to the patient's adjacent or contra-lateral teeth. When stored on a tangible medium, such as a computer diskette, the dental professional can simply forward the diskette to the laboratory for use by the technician. When the data are stored electronically on a computer, electronic files can be forwarded to the technician by e-mail. Using this information, the lab technician may construct a veneer of porcelain or other material, or can determine the proper shade to color the teeth. Each comparison can be electronic by software analysis or by visual comparison if the need arises, e.g., loss of electricity.

After the teeth have been imaged, the dental professional can prepare the teeth to receive the necessary restorations. After the tooth or teeth have been prepared to receive the restoration(s), an image of the prepared teeth can be taken and forwarded to the technician for use in connection with the formulation of the proper size and color of a ceramic buildup or other suitable material. The technician can also take into consideration the color of the prepared tooth when preparing the restoration. The inclusion of the shade of the prepared tooth can be incorporated into the final color calculations so that the closest match can be made.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. An apparatus for scanning an oral environment of a patient, comprising:
    a mouthpiece;
    a scanning device disposed within the mouthpiece and capable of moving within the mouthpiece to simultaneously capture one or more images from both an upper portion and a lower portion of the oral environment; and
    an electronic storage device for storing each image of the oral environment, the storage device being connected to the scanning device.

2. The apparatus of claim 1, wherein the scanning device comprises a camera which is capable of moving within the mouthpiece to provide a complete image of the oral environment.

3. The apparatus of claim 1, further comprising one or more mirrors slidably or rotatably attached to the mouthpiece to redirect images at various angles into the scanning device.

4. The apparatus of claim 1, wherein the electronic storage device comprises a CD, a DVD, digital tape, a computer hard drive, a flash card, a smart card, or an electronic diskette.

5. The apparatus of claim 1, wherein the electronic storage device captures each image for storage on photographic paper or a negative thereof.

6. The apparatus of claim 1, wherein the mouthpiece comprises a tab for a patient having teeth to bite on to temporarily hold the apparatus in a desired position adjacent the patient's teeth.

7. The apparatus of claim 1, wherein the mouthpiece comprises a track within which the scanning device moves.

8. The apparatus of claim 1, which further comprises a monitor to display the captured image.

9. The apparatus of claim 1, wherein the one or more images of the oral environment includes gingival color, gingival height, tooth color, tooth height, and tooth width of each tooth.

10. The apparatus of claim 1, wherein the scanning device is a camera and the storage device comprises a computer and associated printer.

11. An apparatus for obtaining and manipulating electronic images of a plurality of a patient's teeth which comprises:
    a mouthpiece;
    a scanning device disposed within the mouthpiece and capable of moving within the mouthpiece to simultaneously scan a plurality of both upper and lower teeth to provide one or more electronic images that includes the dental characteristic of gingival color, gingival height, tooth color, tooth height, and tooth width of each tooth of the plurality of teeth; and
    an electronic storage device for storing each image of the oral environment, the storage device being electronically connected to the scanning device.

12. The apparatus of claim 11, wherein the scanning device comprises a camera and the electronic storage device comprises a CD, a DVD, digital tape, a computer hard drive, a flash card, a smart card, or an electronic diskette.

13. The apparatus of claim 11, further comprising a processor for analyzing the one or more electronic images.

14. The apparatus of claim 13, wherein the processor compares at least one dental characteristic of one of the electronic images to at least one dental characteristic of either another of the electronic images or to a dental standard image.

15. The apparatus of claim 13, wherein the processor determines the dimensions of the patient's tooth.

16. The apparatus of claim 13, wherein the processor calculates the ratios of the heights and widths of at least two of the plurality of teeth in the electronic image with respect to each other.

17. The apparatus of claim 16, wherein the display device displays the image concurrently with the transferring to the electronic storage device.

18. The apparatus of claim 16, wherein the display device simultaneously displays a plurality of electronic images.

19. The apparatus of claim 13, wherein the processor compares an electronic image including
    the gingival color and gingival height of each tooth with
        a prior electronic image of the same.

20. The apparatus of claim 13, wherein the processor matches the tooth color of at least one tooth of the first electronic image to the color of an adjacent or contra-lateral tooth to facilitate restoration of the at least one tooth.

21. The apparatus of claim 13, wherein the processor comprises a software package.

22. The apparatus of claim 11, further comprising a display device for displaying the electronic images.

* * * * *